United States Patent [19]
Bertolini et al.

[11] Patent Number: 5,905,090
[45] Date of Patent: May 18, 1999

[54] ANALOGUES OF THE ACTIVE METABOLITE OF LEFLUNOMIDE

[75] Inventors: Giorgio Bertolini; Mauro Biffi; Flavio Leoni; Maria Letizia Marchetti; Jacques Mizrahi; Flavio Somenzi; Paolo Mascagni, all of Cinisello Balsamo, Italy

[73] Assignee: Italfarmaco S.p.A., Milan, Italy

[21] Appl. No.: 09/067,982

[22] Filed: Apr. 29, 1998

[51] Int. Cl.$^6$ .................. A61K 31/275; C07C 255/51
[52] U.S. Cl. .................. 514/522; 549/291; 549/318; 558/418; 558/422; 564/158; 514/621; 514/522
[58] Field of Search .................. 558/418, 422; 549/291, 318; 564/158; 514/522, 133, 621

[56] References Cited

PUBLICATIONS

Journal of Medicinal Chemistry, 1977, 40(13) 2011–2016, Giorgio Bertolini et al.

*Primary Examiner*—Johann Richter
*Assistant Examiner*—Ebenezer Sackey
*Attorney, Agent, or Firm*—Griffin, Butler Whisenhunt & Szipl, LLP

[57] ABSTRACT

Analogues of the active metabolite of leflunomide, and to the use thereof as immunosuppressive and/or antinflammatory agents.

3 Claims, No Drawings

ANALOGUES OF THE ACTIVE METABOLITE OF LEFLUNOMIDE

The present invention relates to analogues of the active metabolite of leflunomide, and to the use thereof as immunosuppressive and/or antiinflammatory agents.

BACKGROUND OF THE INVENTION

Leflunomide, i.e. [5-methyl-N-(4-trifluoromethylphenyl) isossazole-4-carboxamide), is a molecule described in EP-B-0 013 376 as an antinflammatory, analgesic and antipyretic agent in the treatment of rheumatoid arthritis, as it also has immunosuppressive activity. Ann. Rep. Med. Chem., 18, 177 (1983) states that its activity is actually exerted by a metabolite, A-77-1726 [N-(4-trifluoromethylphenyl)-1-cyano-2-ketopropyl-carboxamide], in particular by the β-ketonitrile system (which is liable to keto-enol tautomerism) contained therein. In fact, when replacing the cyano group with an ester group, the activity dramatically decreases or even disappears [(J. Chem. Soc. Perkin Trans, 1, 2203 (1992)].

SUMMARY OF THE INVENTION

Now it has surprisingly been found that some analogues of the metabolite A-77-1726, although lacking in the β-ketonitrile system, exert antiinflammatory and immunosuppressive activities, which activities are, in some molecules of the class object of the present invention, separated.

Therefore, the present invention relates to compounds of formula I

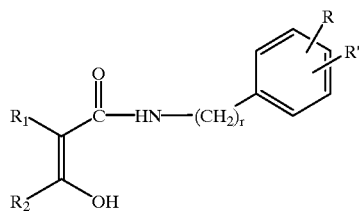

I wherein R and R' are independently a straight or branched ($C_{1-4}$)alkyl, halogen, nitro, cyano, trifluoromethyl, trifluoromethoxy group; r is 0 or 1; $R_1$ is a group

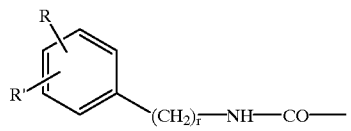

wherein R, R' and r are as defined above; $R_2$ is a straight or branched ($C_{1-4}$) alkyl group; or $R_1+R_2$ are the groups

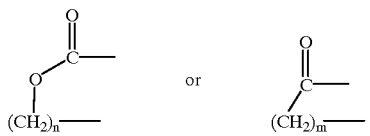

wherein n is 1 or 2, and m is 2 or 3, wherein the carbonyl group is linked to the carbon atom which is in its turn bound to the carbamoyl group; or $R_1+R_2$, together with the carbon atoms they are linked to, form a benzene ring, optionally substituted with halogens, alkoxy or hydroxy groups; the possible keto-enol forms thereof as well as the diastereomers thereof.

DESCRIPTION OF PREFERRED EMBODIMENTS

In the following, "alkyl groups" preferably means methyl, ethyl, propyl, i-propyl, butyl, 2-methylpropyl, n-pentyl, 3-methylbutyl, i-pentyl and the like.

The compounds of the invention are prepared according to techniques known to those skilled in the art. For example, compounds of formula I wherein $R_1$ is the N-phenyl-carboxamide residue defined above and $R_2$ is an alkyl group as defined above, are prepared starting from a compound of formula II

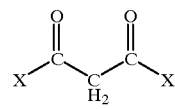

II wherein X is chlorine or bromine, which is reacted with the suitable primary aniline, in the presence of a strong organic base such as a tertiary amine, to give the compound of formula III

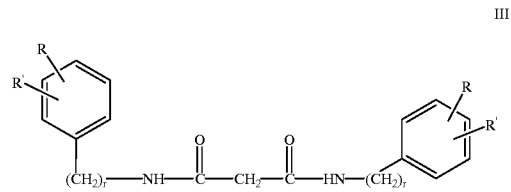

III wherein R, R' and r are as defined above, which is, in its turn, acetylated by treatment with strong bases such as sodium hydride, lithium-diisopropylamide, sodium ethoxide, potassium tert-butoxide, and an acylating agent such as ($C_{1-4}$) acyl-imidazole, acetic, propionic, butyric, pentanoic anhydrides, ($C_{1-4}$)acid chloride, in ether solvents such as tetrahydrofuran (THF), ethyl ether, dioxane, at temperatures ranging from about −15° C. to the reflux temperature of the reaction solvent, for a period of time from about 10 minutes to about 24 hours.

The compounds of formula I wherein R, R' and r are as defined above and $R_1+R_n$ are the groups

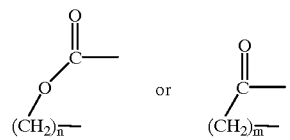

as defined above, are prepared starting from the compound of formula IV

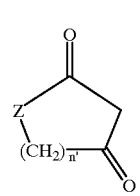

IV wherein Z is an oxygen atom or methylene, and n' is the same as n defined above, which is a commercially available product or can be prepared according to techniques well-known to those skilled in the art. This compound is treated with a strong base such as sodium hydride, lithium-diisopropylamide, sodium ethoxide, potassium tert-butoxide, and a suitable isocyanate, for example trifluoromethylphenylisocyanate, in ether solvents such as THF, ethyl ether, dioxane, at temperatures ranging from about −15° C. to the reflux temperature of the reaction solvent, for a period of time from about 10 minutes to about 24 hours.

The compounds of formula I wherein R, R' and r are as defined above and $R_1+R_2$, together with the carbon atoms they are linked to, form a benzene ring, are obtained starting from an acetylsalicyclic acid reactive derivative such as an acid chloride or a mixed anhydride, which is reacted with the suitable aniline in inert solvents, such as methylene chloride, chloroform, THF, at a temperature ranging from about −15° C. to the reflux temperature of the reaction solvent, for a period of time ranging from about 10 minutes to about 24 hours. The resulting intermediate of formula V

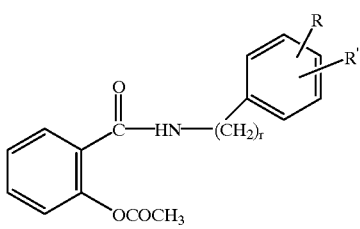

V wherein R, R' and r are as defined above, is transformed into the desired compound of formula I by deacetylation with weak bases such as imidazole or sodium bicarbonate, in water-alcohol solvents such as methanol, ethanol and mixtures thereof with water.

The invention is illustrated in further detail by the following examples.

Experimental section

Melting points were determined on a Buchi apparatus in glass capillary tubes and are uncorrected. Thin-layer chromatography was performed on silica gel glass-backed plates (5719) (E. Merck & Co.), and flash chromatography was performed on silica gel 60 (230–400 mesh ASTM) (E. Merck & Co.). $^1$H and $^{13}$C NMR spectra were recorded on a Varian Gemini 200 spectrometer at 200 MHz and 50.3 MHz respectively, and the chemical shifts are given in ppm δ referenced to DMSO-d6 (2.50 ppm for the $^1$H NMR spectra and 39.5 ppm for the $^{13}$C NMR). Elemental analyses were carried out on Perkin Elmer 240.

EXAMPLE 1

N-(4-trifluoromethylphenyl)-2-(4-trifluoromethylphenylcarbamoyl)-3-hydroxybut-2-enamide A) Malonyl dichloride (13.8 ml, 142 mmol) was slowly added at 0° C. to a solution of 4-trifluoromethylaniline (42.6 ml, 340 mmol) and triethylamine (39.4 ml, 284 mmol) in dichloromethane (500 ml). The mixture was stirred overnight at room temperature, then poured into ethyl acetate (1000 ml) and washed successively with water (500 ml), 1N NaOH (500 ml) and 3N HCl (3×500 ml). The organic phase was dried with anhydrous sodium sulphate and evaporated under reduced pressure giving 53 g (95%) of pure N,N-di(4-trifluoromethylphenyl)malondiamide as a yellow solid: m.p. 215–217° C. (dec.); $^1$H NMR (DMSO-d$_6$) d 7.84 (d, 4H), 7.71 (d, 4H), 3.60 (s, 2H).

B) A solution of N,N-di(4-trifluoromethylphenyl)malondiamide (14 g, 36 mmol) in tetrahydrofuran (100 ml) was slowly added at 0° C. to a suspension of sodium hydride (80% oil dispersion ) (2.15 g, 89.5 mmol) in tetrahydrofuran (150 ml). The mixture was stirred at room temperature for 15 minutes, then 1-acetylimidazole (5.9 g, 54 mmol) in tetrahydrofuran (100 ml) was added and the mixture stirred overnight at room temperature. The solution was poured into ethyl acetate (500 ml) and the organic phase washed with 1N HCl (400 ml), dried with anydrous sodium sulphate and evaporated under reduced pressure. The crude product was triturated twice with hot diethyl ether (50 ml) and filtered. This gave 8.45 g (55%) of pure N-(4-trifluoromethylphenyl)-2-(4-trifluoromethylphenylcarbamoyl)-3-hydroxybut-2-enamide as a white solid. m.p. 170–174° C. (dec.)

| Elemental analysis | C | H | N | F |
|---|---|---|---|---|
| Calculated | 52.79 | 3.26 | 6.48 | 26.37 |
| Found | 52.95 | 3.26 | 6.62 | 26.38 |

$^1$H NMR (DMSO-d$_6$) d 10.68 (s, 2H), 7.82 (m, 4H), 7.72 (m, 4H), 5.02 (s, 1H), 2.31 (s, 3H).
$^{13}$C NMR (DMSO-d$_6$) d 199.7, 164.2, 142.5, 126.5, 124.6, 124.0, 119.3, 68.7, 30.0.

EXAMPLE 2

N-(4-trifluoromethylphenyl)-4-hydroxy-2-oxo-(5H)-furan-3-carboxamide

A solution of 4-hydroxy-2(5H)-furanone (1.47 g, 14.7 mmol) in tetrahydrofuran (30 ml) was slowly added at 0° C. to a suspension of sodium hydride (80% oil dispersion) (530 mg, 14.7 mmol) in tetrahydrofuran (30 ml). The mixture was stirred at room temperature for 15 minutes, then a solution of 4-trifluoromethylphenyl isocyanate (2.75 g, 14.7 mmol) in tetrahydrofuran (20 ml) was added and the mixture stirred overnight at room temperature. At the end of the reaction, the insoluble product was filtered off and the solvent removed under reduced pressure. Crude product was suspended in water (60 ml) and methanol (6 ml) and the mixture acidified to pH 2 with concentrated HCl; the solid thus obtained was filtered and crystallised from acetone giving 1.75 g (41%) of pure N-(4-trifluoromethylphenyl)-4-hydroxy-2-oxo-(5H)-furan-3-carboxamide as a white solid. m.p.204–206° C. (dec.)

| Elemental analysis | C | H | N | F |
|---|---|---|---|---|
| Calculated | 50.19 | 2.81 | 4.88 | 19.85 |
| Found | 50.10 | 2.75 | 4.85 | 19.98 |

$^1$H NMR (DMSO-d$_6$) d 11.50 (s, 1H), 10.23 (s, 1H), 7.83 (m, 2H), 7.65 (m, 2H), 4.71 (s, 2H). $^{13}$C NMR (DMSO-d$_6$) d 187.6, 173.5, 160.2, 142.5, 126.3, 124.6, 123.3, 119.9, 92.7, 68.1.

EXAMPLE 3

N-(4-trifluoromethylphenyl)-2-hydroxy-5-oxocyclopentanecarboxamide

This compound was obtained as a white solid (Yield 32%) starting from 1,3-cyclopentanedione and using the same procedure described in example 2.

m.p.=212–214° C. (dec.)

| Elemental analysis | C | H | N | F |
|---|---|---|---|---|
| Calculated | 54.74 | 3.53 | 4.91 | 19.98 |
| Found | 54.39 | 3.57 | 4.86 | 20.05 |

$^1$H NMR (DMSO-$d_6$) d 10.53 (s, 1H), 7.85 (m, 2H), 7.71 (m, 2H), 2.26 (s, 4H).
$^{13}$C NMR (DMSO-$d_6$) d 201.2, 162.5, 141.8, 126.5, 124.6, 123.9, 119.9, 108.2, 30.84.

EXAMPLE 4

N-(4-trifluoromethylphenyl)-2-hydroxy-6-oxocyclohexanecarboxamide

This compound was obtained as a white solid (Yield 38%) starting from 1,3-cyclohexanedione and using the same procedure described in example 2.

m.p.=125–127° C. (dec.)

| Elemental analysis | C | H | N | F |
|---|---|---|---|---|
| Calculated | 56.19 | 4.04 | 4.68 | 19.05 |
| Found | 56.53 | 4.13 | 4.61 | 18.79 |

$^1$H NMR (DMSO-$d_6$) d 12.78 (s, 1H), 7.81 (m, 2H), 7.75 (m, 2H), 2.64 (m, 4H), 1.95 (m, 2H).
$^{13}$C NMR (DMSO-$d_6$) d 197.0, 169.9, 140.4, 126.6, 125.1, 124.4, 121.4, 103.4, 34.4, 18.9.

EXAMPLE 5

N-(4-trifluoromethylphenyl)-2-hydroxy-benzamide

A) Acetylsalicyclic acid (10 g, 55 mmol) was added to thionyl chloride (8.1 ml, 110 mmol) and the suspension refluxed to complete dissolution of the acid. The yellow solution was then cooled at room temperature and thionyl chloride evaporated under reduced pressure. Crude acyl chloride was dissolved in chloroform and the solvent removed under reduced pressure to give a reddish oil. This procedure was repeated three times. The oil was dissolved in dichloromethane (100 ml) and the resulting solution slowly added at 0° C. to a solution of 4-trifluoromethylaniline (6.3 ml, 50 mmol) and triethylamine (23 ml, 166 mmol) in dichloromethane (100 ml). The mixture was stirred overnight at room temperature then the organic solution was washed successively with 1N HCl (2×200 ml), 1N NaOH (200 ml) and water (200 ml). The organic phase was dried with anhydrous sodium sulphate and evaporated under reduced pressure. The crude product was purified by flash chromatography on silica gel (eluent n-hexane-ethyl acetate 8:2) giving 13 g (80%) of pure N-(4-trifluoromethylphenyl)-2-acetoxy-benzamide as a white solid.

m.p. 210–212° C.
$^1$H NMR (DMSO-$d_6$) d 10.74 (s, 1H), 7.97 (d, 2H), 7.74 (d, 3H), 7.63 (t, 1H), 7.45 (t, 1H), 7.30 (d, 1H), 2.22 (s, 3H).

B) Imidazole (960 mg, 14 mmol) was added to N-(4-trifluoromethylphenyl)-2-acetoxy-benzamide (13 g, 40 mmol) in methanol (300 ml) and the solution stirred at room temperature for two hours. The white precipitate was filtered and dried giving 7.3 g (65%) of pure N-(4-trifluoromethylphenyl)-2-hydroxy-benzamide as a white solid.

m.p. 212–214° C.

| Elemental analysis | C | H | N | F |
|---|---|---|---|---|
| Calculated | 59.79 | 3.58 | 4.98 | 20.27 |
| Found | 59.93 | 3.64 | 4.94 | 20.09 |

$^1$H NMR (DMSO-$d_6$) d 11.51 (s, 1H), 10.67 (s, 1H), 7.98 (m, 2H), 7.93 (dd, 1H), 7.75 (m, 2H), 7.47 (m, 1H), 7.02 (d, 1H), 7.00 (t, 1H).
$^{13}$C NMR (DMSO-$d_6$) d 166.9, 158.1, 142.3, 134.0, 129.6 126.3, 124.6, 124.2, 120.8, 119.5, 118.5, 117.4.

EXAMPLE 6

N-(4-trifluoromethylphenyl)-2-hydroxy-5-methoxybenzamide

This compound was obtained as a white solid starting from 2-hydroxy-5-methoxybenzoic acid and using the same procedure described in example 5.

m.p. 210–211° C.

| Elemental analysis | C | H | N |
|---|---|---|---|
| Calculated | 57.88 | 3.89 | 4.50 |
| Found | 58.33 | 3.89 | 4.38 |

$^1$H NMR (DMSO-$d_6$) d 11.50 (s, 1H), 10.61 (s, 1H), 7.96 (d, 2H), 7.75 (d, 2H), 7.47 (d, 1H), 7.10 (dd, 1H), 6.96 (d, 1H), 3.78 (s, 3H).

EXAMPLE 7

N-(4-trifluoromethylphenyl)-2-hydroxy-5-chlorobenzamide

This compound was obtained as a white solid starting from 2-hydroxy-5-chlorobenzoic acid and using the same procedure described in example 5.

m.p. 220–221° C.

| Elemental analysis | C | H | N | Cl |
|---|---|---|---|---|
| Calculated | 53.27 | 2.87 | 4.44 | 11.23 |
| Found | 53.35 | 2.85 | 4.35 | 11.10 |

$^1$H NMR (DMSO-$d_6$) d 11.47 (s, 1H), 10.69 (s, 1H), 7.96 (d, 2H), 7.90 (d, 1H), 7.75 (d, 2H), 7.49 (dd, 1H), 7.05 (d, 1H).

EXAMPLE 8

N-(4-trifluoromethylphenyl)-2,6-dihydroxybenzamide

This compound was obtained as a white solid starting from 2,6-dihydroxybenzoic acid and using the same procedure described in example 5.

m.p. 226–227° C.

| Elemental analysis | C | H | N | F |
|---|---|---|---|---|
| Calculated | 56.57 | 3.39 | 4.71 | 19.18 |
| Found | 56.66 | 3.42 | 4.66 | 19.09 |

$^1$H NMR (DMSO-$d_6$) d 11.63 (s, 2H), 10.59 (s, 1H), 7.92 (d, 2H), 7.75 (d, 2H), 7.22 (t, 1H), 6.46 (d, 2H).

EXAMPLE 9

N-(4-trifluoromethylphenylmethyl)-2-hydroxybenzamide

This compound was obtained as a white solid starting from acetylsalicyclic acid and 4-trifluoromethylbenzylamine using the same procedure described in example 5.

m.p. 163–165° C.

| Elemental analysis | C | H | N | F |
|---|---|---|---|---|
| Calculated | 61.02 | 4.10 | 4.74 | 19.30 |
| Found | 60.81 | 3.99 | 4.67 | 19.18 |

$^1$H NMR (DMSO-$d_6$) d 11.50 (s, 1H), 9.45 (s, 1H), 7.91 (dd, 1H), 7.73 (d, 2H), 7.77 (d, 2H), 7.42 (m, 1H), 6.93 (m, 2H), 4.62 (d, 2H).

EXAMPLE 10

N-(4-bromophenyl)-2-hydroxybenzamide

This compound was obtained as a white solid starting from acetylsalicyclic acid and 4-bromoaniline using the same procedure described in example 5.

m.p. 173–175° C.

| Elemental analysis | C | H | N | Br |
|---|---|---|---|---|
| Calculated | 53.45 | 3.45 | 4.79 | 27.35 |
| Found | 53.48 | 3.43 | 4.82 | 27.44 |

$^1$H NMR (DMSO-$d_6$) d 11.51 (s, 1H), 10.55 (s, 1H), 7.94 (dd, 1H), 7.72 (d, 2H), 7.57 (d, 2H), 7.45 (m, 1H), 6.96 (m, 2H).

EXAMPLE 11

N-(3-bromophenyl)-2-hydroxybenzamide

This compound was obtained as a white solid starting from acetylsalicyclic acid and 3-bromoaniline using the same procedure described in example 5.

m.p. 190–191° C.

| Elemental analysis | C | H | N | Br |
|---|---|---|---|---|
| Calculated | 53.45 | 3.45 | 4.79 | 27.35 |
| Found | 53.33 | 3.40 | 4.81 | 27.35 |

$^1$H NMR (DMSO-$d_6$) d 11.55 (s, 1H), 10.57 (s, 1H), 8.09 (s, 1H), 7.92 (dd, 1H), 7.67 (m, 1H), 7.46 (m, 1H), 7.35 (m, 2H), 6.99 (m, 2H).

EXAMPLE 12

N-(3-trifluoromethylphenyl)-2-hydroxybenzamide

This compound was obtained as a white solid starting from acetylsalicyclic acid and 3trifluoromethylaniline using the same procedure described in example 5.

m.p. 190–193° C.

| Elemental analysis | C | H | N | F |
|---|---|---|---|---|
| Calculated | 59.79 | 3.58 | 4.98 | 20.27 |
| Found | 59.54 | 3.59 | 5.00 | 20.00 |

$^1$H NMR (DMSO-$d_6$) d 11.58 (s, 1H), 10.63 (s, 1H), 8.25 (s, 1H), 7.96 (m, 2H), 7.63 (t, 1H), 7.47 (m, 2H), 7.00 (m, 2H).

EXAMPLE 13

N-(3-trifluoromethoxyphenyl)-2-hydroxybenzamide

This compound was obtained as a white solid starting from acetylsalicyclic acid and 3trifluoromethoxyaniline using the same procedure described in example 5.

m.p. 163–165° C.

| Elemental analysis | C | H | N | F |
|---|---|---|---|---|
| Calculated | 56.57 | 3.39 | 4.71 | 19.18 |
| Found | 56.73 | 3.43 | 4.71 | 19.26 |

$^1$H NMR (DMSO-$d_6$) d 11.53 (s, 1H), 10.67 (s, 1H), 7.93 (m, 2H), 7.70 (d, 1H), 7.47 (m, 2H), 7.12 (dd, 1H), 6.99 (m, 2H).

EXAMPLE 14

N-(4-trifluoromethoxyphenyl)-2-hydroxybenzamide

This compound was obtained as a white solid starting from acetylsalicyclic acid and 4trifluoromethoxyaniline using the same procedure described in example 5.

m.p. 177–180° C.

| Elemental analysis | C | H | N | F |
|---|---|---|---|---|
| Calculated | 56.57 | 3.39 | 4.71 | 19.18 |
| Found | 56.44 | 3.40 | 4.70 | 19.29 |

$^1$H NMR (DMSO-$d_6$) d 11.58 (s, 1H), 10.59 (s, 1H), 7.93 (m, 3H), 7.42 (m, 3H), 6.99 (m, 2H).

EXAMPLE 15

N-(4-isopropylphenyl)-2-hydroxybenzamide

This compound was obtained as a white solid starting from acetylsalicyclic acid and 4isopropylaniline using the same procedure described in example 5.

m.p. 116–118° C.

| Elemental analysis | C | H | N |
|---|---|---|---|
| Calculated | 75.27 | 6.71 | 5.49 |
| Found | 74.93 | 6.74 | 5.41 |

$^1$H NMR (DMSO-$d_6$) d 11.53 (s, 1H), 10.63 (s, 1H), 8.00 (dd, 1H), 7.63 (d, 2H), 7.46 (dt, 1H), 7.25 (d, 2H), 6.99 (m, 2H), 2.89 (m, 1H), 1.21 (d, 6H).

Mixed lymphocyte reaction (MLR).

The results obtained are reported in Tab. 1.

Bi-directional MLR was carried out using murine cells. Splenocytes were prepared from BALB/c and DBA/2 mice (18–20 g) Charles River, Calco, Italy). Briefly, single cell suspensions were isolated from spleen by Ficoll-Hypaque (biochrom, Berlin, Germany) density gradient centrifugation. $5\times10^4$ splenocytes from each preparation was cultured for 96 hours in triplicate in 96-well round-bottom plates (Nunc, Roskilde, Denmark), in the absence or presence of serial dilutions of the tested compounds. All compounds were dissolved in dimethyl sulfoxide (DMSO) to a final 20 mM concentration and then diluted into the culture medium used for the cell assay. To take into account a possible interference from DMSO, each experiment included a control in which the DMSO concentration was made equal to those of compound-treated cultures. Culture medium used was RPMI 1640 (Biochrom, Berlin, Germany), supplemented with 5% foetal bovine serum (Hyclone Laboratories Inc., Logan, Utah), 50 µm 2-mercaptoethanol, 2 mM L-glutamine, 0.1 mM non-essential amino acids, 1 mM sodium pyruvate, 100 IU/ml penicillin, and 100 µg/ml streptomycin. During the last 18 hours of culture, cells were pulsed with 1 µCi of [$^3$H]-thymidine (Amersham, UK) and then harvested onto glass fiber filters by means of a cell harvester. Radioacivity, proportional to proliferation, was measured with a β-counter. Inhibitory acitvity was expressed as $IC_{50}$, i.e. the concentration of compound that exerted 50% inhibition of proliferation with respect to that of untreated control cultures.

Inhibition of lymphocyte activation antigens expression. The results obtained are reported in Tab. 2.

Human peripheral blood mononuclear cells (PBMC) from healthy donors were separated by Ficoll-Hypaque density-gradient centrifugation. The cells recovered were suspended in culture medium (RPMI 1640 supplemented with 10% foetal bovine serum, 2 mM L-glutamine, 100 IU/ml penicillin and 100 µg/ml streptomycin).

PBMC, suspended at a density of $10^6$ cells/ml in culture medium, were incubated in 24-well plates (Costar, Cambridge, Mass.) with the tested compounds and, 30 min later, stimulated with optimal concentration of the monoclonal antibodies OKT3 (Ortho Diagnostic Inc., Raritan, N.J.) for 24 hr at 37° C. and under 5% $CO_2$. At the end of incubation, cells were washed twice with PBS containing 2% human serum (Irvine Scientific, Irvine, Calif.) and then incubated with fluorescein isothiocyanate (FITC)-conjugated monoclonal antibodies (Mab) for 30 min on ice. Cells were then washed as above and fluorescence analysis was performed by flow-cytometry on a FACScan (Becton-Dickinson, Mountain View, Calif.). The Mabs used were anti-Leu5b (CD2), anti-Interleukin-2 receptor (CD25) and anti transferrin receptor (CD71). Fluorescence background was determined by incubating the cells with FITC-conjugated mouse IgG of the relevant isotype. Forward- and right-angle scatter were set in order to include lymphocytes and lymphoblasts. The results, expressed as percentage of inhibition of mean fluorescence (MF), were calculated as follows:

$$\text{Inhibition} = 100 - \frac{MF(OKT3 + \text{compound}) - MF(\text{control} + \text{compound})}{MF(OKT3) - MF(\text{control})} \times 100$$

Antigen-induced paw edema in the mouse.
The results obtained are reported in Tab. 3.

Groups of 4–8 female BALB/c mice (20–22 g; Charles River, Calco, Italy) were immunised at days 0 and 7 with two s.c. injections, of keyhole limpet hemocyanin (KLH, 100 µg/mouse; Sigma Chemicals, S. Louis, Mo.) emulsified in 0.2 ml complete Freund's adjuvant (CFA, Sigma Chemicals, S. Louis, Mo.). Non-immunised mice (Control) were treated with CFA alone. On day 14, immunised mice were challenged in the hind footpad with 20 µg KLH suspended in physiological solution. Eight hours after antigen challenge the edema was quantified measuring the dorsal-ventral thickness of the footpad with a scientific micrometer (Borletti, Italy). To evaluate their immunosuppressive activity, the compounds were administered daily from day 0 to day 13. Example 5, dissolved in DMSO, was administered i.p.; Leflunomide, suspended in carboxymethylcellulose, was administered p.o.; Cyclosporin A was dissolved in physiological solution containing 18% ethyl alcohol and 2% Tween 80 and administered i.p. the potencies of the compounds were expressed as percentage of inhibition of edema formation calculated as follows:

$$\text{Inhibition} = 100 - \frac{\text{thickness of immunised mice treated with compounds} - \text{thickness of control mice}}{\text{thickness of immunised mice} - \text{thickness of control mice}} \times 100$$

Adjuvant arthritis in the rat

The results obtained are reported in Tab. 4. Male Lewis rats (175 25 g,) were obtained from Charles River (Calco, Italy) and maintained under standard housing conditions (60% humidity and 21 2 C) with free access to food and water and used after at least 5 days acclimatization. Animals were divided into groups of 6. Arthritis was induced by i.d. injection of 0.2 ml complete Freund's adjuvant (CFA) in the hind foot pad. CFA was prepared by suspending heat-inactivated *Mycobacterium tuberculosis* strain H37 RA (Difco, Detroit, USA) in incomplete Freund's adjuvant at 10 mg/ml final concentration. Development of arthritis was evaluated every three days and expressed as clinical scores by a method that takes into account ears, paws and tail on a 0–2 scale for each anatomical district. The sum of arthritic scores was taken as the severity score.

Example 3 was resuspended in carboxymethyl cellulose and administered p.o. daily. Control animals received carboxymethyl cellulose alone.

TABLE 1

Immunosuppressive activity of examples 1, 2, 3, 4, 5 and Leflunomide

| Compound | Mixed lymphocyte reaction $IC_{50}$ (µM) |
|---|---|
| Example 1 | 11.9 ± 0.1 |
| Example 2 | 3.4 ± 1.1 |
| Example 3 | 1.25 ± 0.2 |
| Example 4 | 45.9 ± 29.5 |
| Example 5 | 1.65 ± 0.1 |
| Leflunomide | 9.6 ± 3.1 |

TABLE 2

Activity of examples 1, 2, 3, 4, 5 and Leflunomide on the expression of CD2, CD25 and CD71 lymphocyte activation antigens

| Compound | CD2 expression $IC_{50}$ (µM) | CD25 expression $IC_{50}$ (µM) | CD71 expression $IC_{50}$ (µM) |
|---|---|---|---|
| Example 1 | 15.3 | 18.4 | 18.8 |
| Example 2 | 13.8 | 14.8 | 66.5 |
| Example 3 | 2.9 | 2.9 | 11.0 |
| Example 4 | 95.4 | >100 | >100 |
| Example 5 | 3.0 | 2.4 | 4.4 |
| Leflunomide | 125.6 | 130.0 | >100 |

TABLE 3

Immunosuppressive activity of example 5, Leflunomide and Cyclosporin A on antigen-induced paw edema formation in the mouse

| Compound | Dose (mg/Kg) | Percentage of inhibition of edema formation |
| --- | --- | --- |
| Example 5 | 10 | 37 |
| Leflunomide[a] | 10 | 43 |
| Cyclosporin A | 5 | 47 |
| Cyclosporin A | 50 | 82 |

[a]Administered p.o.

TABLE 4

Effect of example 3 on development of adjuvant arthritis in the rat

| | Day 14 | | Day 17 | | Day 21 | |
| --- | --- | --- | --- | --- | --- | --- |
| | Score | Inhibition (%) | Score | Inhibition (%) | Score | Inhibition (%) |
| Vehicle | 3.6 ± 0.5 | | 4.8 ± 0.4 | | 4.8 ± 0.6 | |
| Example 3 | 2.1 ± 0.1 | 42 | 2.6 ± 0.1 | 46 | 3.9 ± 0.2 | 19 |

We claim:

1. Compounds of formula I

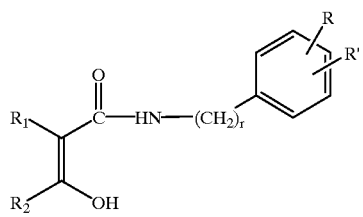

wherein R and R' are independently a straight or branched $(C_{1-4})$alkyl, halogen, nitro, cyano, trifluoromethyl, trifluoromethoxy group; r is 0 or 1; $R_1$ is a group

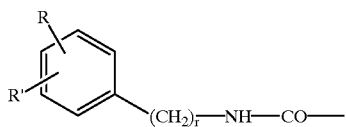

wherein R, R' and r are as defined above; $R_2$ is a straight or branched $(C_{1-4})$ alkyl group; or $R_1+R_2$ are the groups

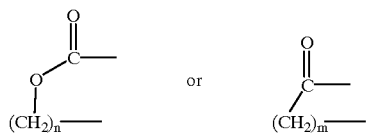

wherein n is 1 or 2, and m is 2 or 3, wherein the carbonyl group is linked to the carbon atom which is in its turn bound to the carbamoyl group; or $R_1+R_2$, together with the carbon atoms they are linked to, form a benzene ring, optionally substituted with halogens, alkoxy or hydroxy groups; the possible keto-enol forms thereof as well as the diastereomers thereof.

2. A pharmaceutical composition containing as the active ingredient at least one compound as claimed in claim 1 together with pharmaceutically acceptable excipients.

3. A method of treating an animal for immunosuppression and inflammation, comprising treating the animal with an immunosuppression or inflammation suppression effective amount of a compound of claim 1.

* * * * *